(12) United States Patent
Blackstone et al.

(10) Patent No.: US 11,970,816 B2
(45) Date of Patent: *Apr. 30, 2024

(54) DUAL SURFACTANT DIGESTER ADDITIVE COMPOSITION AND A METHOD FOR ENHANCING THE PULPING OF WOOD CHIPS USING THE SAME

(71) Applicant: ChemStone, Inc., Greenville, SC (US)

(72) Inventors: Michael M. Blackstone, Jacksonville, FL (US); Peter Spizzirri, Greenville, SC (US)

(73) Assignee: ChemStone, Inc., Greenville, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/399,099

(22) Filed: Aug. 11, 2021

(65) Prior Publication Data

US 2021/0372048 A1  Dec. 2, 2021

Related U.S. Application Data

(62) Division of application No. 15/827,137, filed on Nov. 30, 2017, now Pat. No. 11,091,875.

(60) Provisional application No. 62/428,072, filed on Nov. 30, 2016.

(51) Int. Cl.
| | |
|---|---|
| *D21C 3/06* | (2006.01) |
| *C07C 309/86* | (2006.01) |
| *C08L 71/08* | (2006.01) |
| *D21C 3/20* | (2006.01) |
| *D21C 3/22* | (2006.01) |
| *D21C 7/10* | (2006.01) |
| *D21H 21/24* | (2006.01) |

(52) U.S. Cl.
CPC ............ *D21C 3/222* (2013.01); *C07C 309/86* (2013.01); *C08L 71/08* (2013.01); *D21C 3/06* (2013.01); *D21C 3/20* (2013.01); *D21C 7/10* (2013.01); *D21H 21/24* (2013.01)

(58) Field of Classification Search
CPC . D21C 3/222; D21C 3/06; D21C 3/20; D21C 7/10
USPC .......................................................... 162/72
See application file for complete search history.

(56) References Cited

U.S. PATENT DOCUMENTS

| | | |
|---|---|---|
| 3,078,315 A | 2/1963 | Steele, Jr. et al. |
| 4,906,331 A | 3/1990 | Blackstone et al. |
| 5,032,224 A | 7/1991 | Ahluwalia |
| 5,298,120 A | 3/1994 | Blackstone |
| 5,501,769 A | 3/1996 | Blackstone et al. |
| 5,595,628 A | 1/1997 | Gordon et al. |
| 6,759,382 B2 | 7/2004 | Ahmed |
| 7,807,021 B2 | 10/2010 | Blackstone et al. |
| 8,920,602 B2 | 12/2014 | Blackstone et al. |

*Primary Examiner* — Jacob T Minskey
(74) *Attorney, Agent, or Firm* — Dority & Manning, P.A.

(57) ABSTRACT

In general, the present invention is directed to a method of cooking wood in a cooking liquor medium. The method comprises a step of providing wood to a treatment vessel and contacting the wood with a digester additive composition. The composition comprises a first surfactant comprising an anionic surfactant, a derivative thereof, a salt thereof, or any combination thereof and a second surfactant comprising a polyoxyalkylene glycol or a derivative thereof. Additionally, according to another embodiment, the present invention is directed to a digester additive composition comprising a first surfactant comprising an anionic surfactant, a derivative thereof, a salt thereof, or any combination thereof and a second surfactant comprising a polyoxyalkylene glycol or a derivative thereof.

19 Claims, No Drawings

DUAL SURFACTANT DIGESTER ADDITIVE COMPOSITION AND A METHOD FOR ENHANCING THE PULPING OF WOOD CHIPS USING THE SAME

CROSS-REFERENCE TO RELATED APPLICATIONS

The present application is a divisional of U.S. patent application Ser. No. 15/827,137 having a filing date of Nov. 30, 2017 which claims priority to U.S. Provisional Application Ser. No. 62/428,072 having a filing date of Nov. 30, 2016, both of which are incorporated herein by reference in their entirety.

BACKGROUND

The majority of paper products are produced by a sulfate pulping process known as "Kraft" pulping. The process is characterized by the fact that sodium sulfide is added to the medium that is used to cook wood chips and produce pulp. When this technique was introduced over a century ago, the addition of sodium sulfide produced a dramatic improvement in pulp strength, pulp yield, and durability of the paper made therefrom.

In the typical Kraft digestion process, wood chips are added to an aqueous medium consisting mostly of white liquor which will be transformed into black liquor during the cook. In general, the liquor in which the wood chips are cooked, or cooking liquor, comprises a mixture of black and white liquor, the black liquor being liquor added back to the cooking vessel, or digester, from a prior batch of wood chips and the white liquor being a freshly prepared alkaline solution as described below. Black liquor varies considerably among different mills depending on the white liquor used, the wood employed, and the method of cooking. Typical white liquor is a solution of sodium hydroxide, sodium carbonate, sodium sulfate, sodium sulfide and various inorganic materials. White liquor solubilizes the pulp and removes the lignin from the wood fibers as described below.

During the digestion process, various additives can be employed for providing a pulp and/or resulting paper product with desirable characteristics and properties. Additionally, various additives can also be employed to control or enhance the digestion process. For instance, additives can be employed to improve the pulp yield and/or to reduce the number of extractives. Although various agents and processes have been employed to enhance the cooking of wood pulp, many prior art compositions and methods are deficient in producing a reduction in pulp rejects and an increase pulp yield.

As a result, while current methods and compositions exist, there is always a need for an improvement in the performance of the Kraft process. In particular, there is a need to provide an improved digester additive composition and an improved method of cooking or processing wood during a Kraft process.

SUMMARY

In general, according to one embodiment of the present disclosure, a method of cooking wood in a cooking liquor medium is disclosed. The method comprises a step of providing wood to a treatment vessel and contacting the wood with a digester additive composition. The composition comprises a first surfactant comprising an anionic surfactant and a second surfactant comprising a polyoxyalkylene glycol or a derivative thereof.

In general, according to another embodiment of the present disclosure, a digester additive composition is disclosed. The digester additive composition comprises a first surfactant comprising an anionic surfactant and a second surfactant comprising a polyoxyalkylene glycol or a derivative thereof.

Other features and aspects of the present disclosure are discussed in greater detail below.

DETAILED DESCRIPTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations.

In general, according to one embodiment, the present invention is directed to a method of cooking wood in a cooking liquor medium. The method comprises a step of providing wood to a treatment vessel and contacting the wood with a digester additive composition. The composition comprises a first surfactant comprising an anionic surfactant and a second surfactant comprising a polyoxyalkylene glycol or a derivative thereof. Additionally, according to another embodiment, the present invention is directed to a digester additive composition comprising a first surfactant comprising an anionic surfactant and a second surfactant comprising a polyoxyalkylene glycol or a derivative thereof.

The present inventors have discovered that employing the dual surfactant system as disclosed herein provides various advantages during the pulping process. In particular, the first surfactant and the second surfactant may provide a synergistic effect on a Kraft process when employed in combination. By employing the dual surfactant system, the present inventors have discovered that the composition and/or method disclosed herein may provide an improvement in the pulp yield and/or a reduction in extractives.

For instance, the composition and/or method disclosed herein may provide decker extractives in an average amount of 0.2% or less, such as 0.15% or less, such as 0.14% or less, such as 0.13% or less, such as 0.12% or less, such as 0.11% or less, such as 0.1% or less to 0% or more, such as 0.05% or more. Such average percent of decker extractives may be realized over the course of at least 3 plant runs, such as at least 4 plant runs, such as at least 5 plant runs, such as at least 6 plant runs, such as at least 7 plant runs, such as at least 10 plant runs.

The composition and/or method disclosed herein may provide pulp extractives in an average amount of 0.1% or less, such as 0.06% or less, such as 0.05% or less, such as 0.045% or less, such as 0.04% or less, such as 0.035% or less, such as 0.3% or less to 0% or more, such as 0.01% or more. Such average percent of pulp extractives may be realized over the course of at least 3 plant runs, such as at least 4 plant runs, such as at least 5 plant runs, such as at least 6 plant runs, such as at least 7 plant runs, such as at least 10 plant runs.

For instance, the composition and/or method disclosed herein may provide total (decker and pulp) extractives in an average amount of 0.15% or less, such as 0.1% or less, such as 0.09% or less, such as 0.08% or less, such as 0.07% or less, such as 0.065% or less to 0% or more, such as 0.02% or more, such as 0.03% or more. Such average percent of total (decker and pulp) extractives may be realized over the course of at least 3 plant runs, such as at least 4 plant runs, such as at least 5 plant runs, such as at least 6 plant runs, such as at least 7 plant runs, such as at least 10 plant runs.

In addition, the composition and/or method disclosed herein may provide a reduction in extractives (decker, pulp, or total) by about 1% or more, such as about 2% or more, such as about 5% or more, such as about 10% or more, such as about 20% or more, such as about 30% or more, such as about 35% or more, such as about 40% or more to 80% or less, such as 70% or less, such as 60% or less, such as 50% or less, such as 45% or less. For instance, in one embodiment, such improvement may be in comparison to a process that does not employ the present dual surfactant system. In particular, such improvement may be in comparison to a process that only employs the second surfactant disclosed herein. Further, such improvement may be realized over the course of at least 3 plant runs, such as at least 4 plant runs, such as at least 5 plant runs, such as at least 6 plant runs, such as at least 7 plant runs, such as at least 10 plant runs.

Additionally, the composition and/or method disclosed herein may provide an improvement in the pulp yield by about 0.05% or more, such as about 1% or more, such as about 2% or more, such as about 5% or more, such as about 10% or more to about 20% or less, such as about 15% or less, such as about 10% or less, such as about 5% or less. For instance, in one embodiment, such improvement may be in comparison to a process that does not employ the present dual surfactant system. For instance, such improvement may be in comparison to a process that only employs the second surfactant disclosed herein.

In addition, the time required for pulp absorbency can be reduced substantially. For instance, the average time for pulp absorbency may be 2.5 seconds or less, such as 2.4 seconds or less, such as 2.3 seconds or less, such as 2.2 seconds or less, such as 2.1 seconds or less to 1 second or more, such as 1.5 seconds or more, such as 1.8 seconds or more. Such average time may be realized over the course of at least 3 plant runs, such as at least 4 plant runs, such as at least 5 plant runs, such as at least 6 plant runs, such as at least 7 plant runs, such as at least 10 plant runs.

Additionally, the composition and/or method disclosed herein may provide an improvement in the time for pulp absorbency by about 1% or more, such as about 2% or more, such as about 5% or more, such as about 10% or more, such as about 15% or more to about 40% or less, such as about 30% or less, such as about 25% or less, such as about 20% or less. For instance, in one embodiment, such improvement may be in comparison to a process that does not employ the present dual surfactant system. For instance, such improvement may be in comparison to a process that only employs the second surfactant disclosed herein.

In general, as disclosed above, the first surfactant comprises an anionic surfactant. It should be understood that such anionic surfactant also includes derivatives thereof, salts thereof, or any combinations thereof.

In one embodiment, the first surfactant comprises a sulfonic acid, a sulfate, a carboxylate, a phosphate, or a derivative thereof, a salt thereof, or any combination thereof.

In general, in one embodiment, the first surfactant as disclosed herein includes a sulfonic acid. In one particular embodiment, the first surfactant comprises a sulfonic acid, a derivative thereof, a salt thereof, or any combination thereof. In another particular embodiment, the first surfactant comprises a derivative of sulfonic acid. In another particular embodiment, the first surfactant comprises a salt of sulfonic acid. In another particular embodiment, the first surfactant comprises a salt of a derivative of sulfonic acid.

In one particular embodiment, the first surfactant comprises a benzenesulfonic acid, a derivative thereof, a salt thereof, or any combination thereof. In another embodiment, the first surfactant comprises benzenesulfonic acid or a derivative thereof. In another embodiment, the first surfactant comprises benzenesulfonic acid or a salt thereof.

In one embodiment, the first surfactant comprises benzenesulfonic acid. In another embodiment, the first surfactant comprises a derivative of benzenesulfonic acid. In another embodiment, the first surfactant comprises a salt of benzenesulfonic acid. In another embodiment, the first surfactant comprises a salt of a derivative of benzenesulfonic acid.

As indicated above, in one embodiment, the first surfactant comprises a derivative of benzenesulfonic acid. For instance, in one embodiment, the derivative may be an alkyl derivative, an alkenyl derivative, or an alkynyl derivative. In another embodiment, the derivative may be an alkyl derivative or an alkenyl derivative. In one particular embodiment, the derivative may be an alkyl derivative.

In particular, such derivative may have 2 or more, such as 4 or more, such as 6 or more, such as 8 or more, such as 10 or more to 22 or less, such as 20 or less, such as 18 or less, such as 16 or less, such as 14 or less, such as 12 or less carbon atoms. For instance, such derivative may have from 2 to 22 carbon atoms, such as from 4 to 20 carbon atoms, such as from 6 to 18 carbon atoms, such as from 8 to 14 carbon atoms.

As indicated above, in one embodiment, the first surfactant comprises a salt of benzenesulfonic acid, such as a salt of a derivative of benzenesulfonic acid. The salt may be an alkali metal salt. For instance, the alkali metal may include sodium, potassium, lithium, or any combination thereof. In another embodiment, the alkali metal may include sodium, potassium, or any combination thereof. In one particular embodiment, the alkali metal may include sodium. In one particular embodiment, the alkali metal may include potassium. In one embodiment, the salt may be an ammonium salt.

In one particular embodiment, first surfactant may be a heptylbenzenesfulonic acid, an octylbenzenesulfonic acid, a nonylbenzenesulfonic acid, a decylbenzenesfulonic acid, an undecylbenzenesfulonic acid, a dodecylbenzenesulfonic acid, a tridecylbenzenesulfonic acid, a tetradecylbenzenesfulonic acid, pentadecylbenzenesulfonic acid, sedecylbenzenesulfonic acid, a salt thereof, or any combination thereof. In one particular embodiment, the first surfactant may include dodecylbenzenesulfonic acid, a salt thereof, or any combination thereof. In another particular embodiment, the first surfactant may include a salt of dodecylbenzenesulfonic acid.

In one embodiment, the first surfactant may include a combination of benzenesulfonic acids. For instance, the first surfactant may include a combination of derivatives, or salts thereof, of benzenesulfonic acid. For instance, in one embodiment, the benzenesulfonic acid may include $C_{10}$-$C_{16}$ alkyl derivatives, in particular a salt of the $C_{10}$-$C_{16}$ alkyl derivatives of benzenesulfonic acid.

Alternatively, in one embodiment, the first surfactant may include a benzenesulfonic acid as disclosed herein and a second sulfonic acid, wherein the second sulfonic acid is not a benzenesulfonic acid. For instance, the second sulfonic acid may be a second aromatic sulfonic acid, wherein the second aromatic sulfonic acid is not a benzenesulfonic acid.

In one embodiment, the first surfactant comprises a sulfate, a derivative thereof, a salt thereof, or any combination thereof. In one embodiment, the sulfate may be a derivative, such as an alkyl derivative, an alkenyl derivative, alkynyl derivative, or an alkyl ether derivative. In one embodiment, the derivative may be an alkyl derivative, for instance one having a number of carbon atoms as described above with respect to the derivatives of the sulfonic acids. In another embodiment, the derivative may be an alkyl ether derivative.

In one embodiment, the sulfate may be a salt of the sulfate. For instance, the salt may be an alkali metal salt. For instance, the alkali metal may include sodium, potassium, lithium, or any combination thereof. In another embodiment, the alkali metal may include sodium, potassium, or any combination thereof. In one particular embodiment, the alkali metal may include sodium. In one particular embodiment, the alkali metal may include potassium. In one embodiment, the salt may be an ammonium salt.

In one embodiment, the sulfate may be a salt of a derivative of a sulfate. For instance, such surfactant may be those such as sodium dodecyl sulfate, sodium laureth sulfate, ammonium lauryl sulfate, sodium myreth sulfate and the like.

In one embodiment, the first surfactant comprises a carboxylate, a derivative thereof, a salt thereof, or any combination thereof. In one embodiment, the carboxylate may be a derivative, such as an alkyl derivative, an alkenyl derivative, or alkynyl derivative. In one embodiment, the derivative may be an alkyl derivative, for instance one having a number of carbon atoms as described above with respect to the derivatives of the sulfonic acids.

In one embodiment, the carboxylate may be a salt of the carboxylate. For instance, the salt may be an alkali metal salt. For instance, the alkali metal may include sodium, potassium, lithium, or any combination thereof. In another embodiment, the alkali metal may include sodium, potassium, or any combination thereof. In one particular embodiment, the alkali metal may include sodium. In one particular embodiment, the alkali metal may include potassium. In one embodiment, the salt may be an ammonium salt.

In one embodiment, the carboxylate may be a salt of a derivative of a carboxylate. For instance, such surfactant may be those such as sodium stearate, sodium lauroyl sarcosinate and the like.

In general, as disclosed above, the second surfactant as disclosed herein includes a polyoxyalkylene glycol or a derivative thereof (e.g., esters and diesters of polyoxyalkylene glycols). In one particular embodiment, the second surfactant comprises a polyoxyalkylene glycol or a derivative thereof. For instance, the alkylene may be a $C_2$-$C_5$ alkylene, such as a $C_2$-$C_4$ alkylene, such as a $C_2$-$C_3$ alkylene. For instance, the second surfactant comprises a polyethylene glycol, a polypropylene glycol, a derivative thereof, or any combination thereof.

In one embodiment, the second surfactant comprises a copolymer of the polyoxyalkylene glycol or a derivative thereof. For instance, in one embodiment, the second surfactant comprises a polyethylene glycol-polypropylene glycol copolymer or a derivative thereof. In one particular embodiment, the copolymer is a block copolymer.

For instance, the polyethylene glycol-polypropylene glycol copolymer may be represented by the general formula:

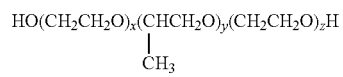

in which x, y, and z are integers having a value of 1 or more. In one particular embodiment, x and/or z is from 1 to 50 and y is from 1 to 100. However, it should be understood that any combination of x, y, and z may be utilized as long as the block copolymers have the desired molecular weight, HLB value, and/or hydrophile percent. The block copolymers are generally described in U.S. Pat. Nos. 2,999,045 and 4,906,331, which are incorporated herein by reference in their entirety.

Specific block copolymers include, but are not limited to, those under the PLURONIC® trademark. These include, but are not limited to, PLURONIC® L-44, PLURONIC® L-62, PLURONIC® L-64, PLURONIC® F-68, PLURONIC® F-108, and PLURONIC® F-127. However, it should be understood that other polyethylene glycol-polypropylene glycol block copolymers may also be employed.

The polyethylene glycol-polypropylene glycol copolymers may have an average molecular weight, in particular a weight average molecular weight, of at least about 500 g/mol, such as about 1,000 g/mol or more, such as about 2,000 g/mol or more, such as about 5,000 g/mol or more, such as about 7,500 g/mol or more, such as about 10,000 g/mol or more and generally about 30,000 g/mol or less, such as about 20,000 g/mol or less, such as about 15,000 g/mol or less, such as about 10,000 g/mol or less, such as about 5,000 g/mol or less, such as about 3,000 g/mol or less. When only one copolymer is employed, such copolymer may satisfy the aforementioned molecular weight ranges. When more than one copolymer is employed, such copolymers may each satisfy the aforementioned molecular weight ranges. In addition, when more than one copolymer is employed, the average molecular weight of such copolymers may also satisfy the aforementioned molecular weight ranges.

The hydrophilic-lipophilic balance (HLB) value is utilized to describe the hydrophilic or lipophilic tendencies of a surfactant molecule. Higher HLB values generally indicate a hydrophilic tendency while lower HLB values generally indicate a lipophilic tendency. The HLB value may also provide an indication of the solubility of a specific surfactant molecule. The polyethylene glycol-polypropylene glycol copolymers may have an HLB value of 2 or more, such as about 3 or more, such as about 4 or more, such as about 5 or more, such as about 10 or more, such as about 15 or more, such as about 20 or more and generally about 30 or less, such as about 25 or less, such as about 20 or less, such as about 15 or less, such as about 10 or less, such as about 7 or less.

In general, the ethylene oxide segments of the copolymer exhibit hydrophilic tendencies. Thus, the copolymers may have a hydrophile percent greater than 10%, such as about 15% or more, such as about 20% or more, such as about 30% or more, such as about 40% or more, such as about 50% or more, such as about 60% or more and generally about 100% or less, such as about 90% or less, such as about 80% or less, such as about 70% or less, such as about 60% or less, such as about 50% or less, such as about 40% or less, based on the total number of propylene glycol and ethylene glycol monomer segments.

In general, the propylene glycol may be present in the copolymers in an amount of about 15% or more, such as about 20% or more, such as about 30% or more, such as about 40% or more, such as about 50% or more, such as about 70% or more and about 100% or less, such as about 90% or less, such as about 85% or less, such as about 80% or less, such as about 70% or less, such as about 60% or less, such as about 50% or less, such as about 40% or less, based on the total number of propylene glycol and ethylene glycol monomer segments.

In one embodiment, the second surfactant comprises a derivative of a polyethylene glycol-polypropylene glycol copolymer. For instance, the second surfactant comprises an ester derivative of a polyethylene glycol-polypropylene glycol copolymer, such as a block copolymer. In one particular embodiment, the second surfactant comprises a diester derivative of a polyethylene glycol-polypropylene glycol copolymer, such as a block copolymer.

For instance, the ester derivative, such as the diester derivative, can be obtained by reacting the copolymer with a carboxylic acid. In one embodiment, the acid may be a fatty acid. Thus, the polyethylene glycol-polypropylene glycol copolymer may be esterified with a fatty acid. In general, any fatty acid may be utilized for the esterification reaction with the polyethylene glycol-polypropylene glycol copolymer.

In one embodiment, the carboxylic acid may be a saturated acid or an unsaturated acid. For instance, the carboxylic acid may be a saturated fatty acid or an unsaturated fatty acid.

In one embodiment, the carboxylic acid, such as the fatty acid, may have at least 4 carbon atoms, such as 8 carbon atoms or more, such as 10 carbon atoms or more, such as 12 carbon atoms or more, such as 15 carbon atoms or more and 30 carbon atoms or less, such as 25 carbon atoms or less, such as 22 carbon atoms or less, such as 20 carbon atoms or less. The carboxylic acids may include, but are not limited to, maleic acid, palmitic acid, stearic acid, adipic acid, abietic acid, linoleic acid, oleic acid, and the like, and any combination thereof.

However, unrefined acids may also be utilized for the esterification reaction with the polyethylene glycol-polypropylene glycol copolymer. These unrefined fatty acids include, but are not limited to, coconut oil, cochin oil, corn oil, cottonseed oil, linseed oil, olive oil, palm oil, palm kernel oil, peanut oil, soybean oil, sunflower oil, tall oils, tallow, *lesquerella* oil, tung oil, whale oil, tea seed oil, sesame seed oil, safflower oil, rapeseed oil, fish oils, avocado oil, mustard oil, rice bran oil, almond oil, walnut oil, derivatives thereof, and combinations thereof.

In one embodiment, the copolymer, such as the block copolymer, may be a $C_4$-$C_{30}$ carboxylic acid modified copolymer, such as a $C_8$-$C_{25}$ carboxylic acid modified copolymer, such as a $C_{10}$-$C_{22}$ carboxylic acid modified copolymer, such as a $C_{15}$-$C_{20}$ carboxylic acid modified copolymer. In one particular embodiment, the carboxylic acid is oleic acid such that the second surfactant comprises an oleate ester, such as a dioleate ester/oleate diester, of a polyethylene glycol-polypropylene glycol copolymer, such as a block copolymer.

In general, the ester derivative of the polyethylene glycol-polypropylene glycol copolymer can be synthesized using any method generally employed in the art. For instance, the esterification process can involve combining the polyethylene glycol-polypropylene glycol copolymer with an acid, such as a fatty acid, in the presence of an acid catalyst. The mixing vessel is agitated under a nitrogen blanket during heating in the range of about 180° C. to about 220° C. Esterification is substantially complete when an acid value (mg KOH/g) of less than about 5.0 is obtained. However, it should be understood that other esterification process may be employed for producing the copolymer derivative. A person of ordinary skill in the art may utilize other esterification reactions to synthesize the ester of the polyethylene glycol-polypropylene glycol copolymer because the invention described herein is not limited to a particular esterification method.

In one embodiment, a combination of second surfactants may be employed. For instance, in one embodiment, a combination of different polyethylene glycol-polypropylene glycol copolymers may be employed. Thus, the additives may include more than one ester of a polyethylene glycol-polypropylene glycol copolymer. In such instances, the polyethylene glycol-polypropylene glycol copolymers, such as the ester derivatives of such copolymers, may be different as long as they have the desired molecular weight, HLB value, and hydrophile percent.

For example, the composition may comprise a first polyethylene glycol-polypropylene glycol copolymer or a derivative thereof and a second polyethylene glycol-polypropylene glycol copolymer or a derivative thereof. The first polyethylene glycol-polypropylene glycol copolymer or a derivative thereof may have a molecular weight of from about 1,000 g/mol to about 5,000 g/mol, such as from about 2,000 g/mol to about 4,000 g/mol and/or a hydrophile percent of greater than 10% to less than about 35%, such as greater than 15% to less than about 25%. The second polyethylene glycol-polypropylene glycol copolymer or a derivative thereof may have a molecular weight of from about 10,000 g/mol to about 15,000 g/mol, such as from about 12,000 g/mol to about 14,000 g/mol and/or a hydrophile percent of greater than about 60% to less than about 80%, such as greater than about 65% to less than about 75%.

Additionally, when more than one copolymer is utilized, they may be employed in the same amounts. Alternatively, they may be employed in different amounts. For instance, the first copolymer may be present with the second copolymer at a weight ratio of from about 10:1 to about 1:10, such as from about 5:1 to about 1:5, such as from about 2:1 to about 1:2, such as at about 1:1.

It should be understood that the combinations provided above are merely two combinations of the polyethylene glycol-polypropylene glycol copolymer or a derivative thereof. It should be understood that any polyethylene glycol-polypropylene glycol copolymers may be combined based on the molecular weight, HLB value, and hydrophile percent specifications provided herein.

In general, the first surfactant and/or second surfactant are employed in an amount in the digester vessel and/or composition to increase the pulp yield and/or reduce the extractives. Generally, they may be employed in an amount to improve the efficiencies of the chemical pulping process.

The first surfactant, the second surfactant, or both in combination may be provided in an amount of about 0.01 wt. % or more, such as about 0.05 wt. % or more, such as about 0.1 wt. % or more, such as about 0.2 wt. % or more, such as 0.3 wt. % or more to about 5 wt. % or less, such as about 2.5 wt. % or less, such as about 2 wt. % or less, such as about 1.5 wt. % or less, such as about 1 wt. % or less, such as about 0.5 wt. % or less, based on the dry weight of the wood.

The weight ratio of the first surfactant to the second surfactant may be about 1:100 or more, such as about 1:75 or more, such as about 1:50 or more, such as about 1:30 or more, such as about 1:20 or more, such as about 1:15 or more, such as about 1:10 or more, such as about 1:9 or more, such as about 1:8 or more, such as about 1:6 or more, such as about 1:5 or more, such as about 1:4 or more, such as about 1:3 or more, such as about 1:2 or more to about 10:1 or less, such as about 5:1 or less, such as about 4:1 or less, such as about 3:1 or less, such as about 2:1 or less, such as about 1.5:1 or less, such as about 1:1 or less, such as about 1:2 or less, such as about 1:3 or less.

In general, the first surfactant can be employed in an amount of about 0.00001 wt. % or more, such as about 0.0001 wt. % or more, such as about 0.0005 wt. % or more, such as about 0.001 wt. % or more, such as about 0.01 wt. % or more, such as about 0.1 wt. % or more, such as about 0.2 wt. % or more, such as about 0.3 wt. % or more, such as about 0.5 wt. % or more, such as about 0.75 wt. % or more, such as about 1 wt. % or more to about 10 wt. % or less, such as about 5 wt. % or less, such as about 4 wt. % or less, such as about 3 wt. % or less, such as about 2 wt. % or less, such as about 1.5 wt. % or less, such as about 1.25 wt. % or less, such as about 1 wt. % or less, such as about 0.5 wt. % or less, such as about 0.2 wt. % or less, such as about 0.1 wt. % or less, based on the dry weight of the wood.

In general, the second surfactant can be employed in an amount of about 0.00001 wt. % or more, such as about 0.0001 wt. % or more, such as about 0.0005 wt. % or more, such as about 0.001 wt. % or more, such as about 0.01 wt. % or more, such as about 0.1 wt. % or more, such as about 0.2 wt. % or more, such as about 0.3 wt. % or more, such as about 0.5 wt. % or more, such as about 0.75 wt. % or more, such as about 1 wt. % or more to about 10 wt. % or less, such as about 5 wt. % or less, such as about 4 wt. % or less, such as about 3 wt. % or less, such as about 2 wt. % or less, such as about 1.5 wt. % or less, such as about 1.25 wt. % or less, such as about 1 wt. % or less, such as about 0.5 wt. % or less, such as about 0.2 wt. % or less, such as about 0.1 wt. % or less, based on the dry weight of the wood.

In general, without intending to be limited by theory, it is believed that the first surfactant may function as a detergent while the second surfactant may function as a wetting agent. For instance, the second surfactant may assist with infiltrating the wood in a more efficient manner thereby allowing for a more efficient pulping process.

In one embodiment, the additive composition may also contain a carrier. For instance, the carrier may be employed for transporting or delivering the first surfactant and/or second surfactant. In one particular embodiment, the carrier comprises water. For instance, the water may be present in an amount of 20 wt. % or more, such as 30 wt. % or more, such as 40 wt. % or more, such as 50 wt. % or more, such as 60 wt. % or more, such as 70 wt. % or more, such as about 80 wt. % or more to less than 100 wt. %, such as about 99 wt. % or less, such as about 95 wt. % or less, such as about 90 wt. % or less, such as about 80 wt. % or less, based on the weight of the additive composition.

As indicated above, the present invention is also directed to a method of cooking wood in a cooking liquor medium. The method comprises a step of providing wood to a treatment vessel and contacting the wood with a digester additive composition as disclosed herein. Accordingly, the method disclosed herein can also be directed to a method of producing pulp from cellulosic materials, such as wood chips.

The wood may be any wood known in the art that is employed in a pulping process. For instance, the wood may include hardwoods, softwoods, or mixtures thereof. In one embodiment, the wood may include primarily coniferous wood (e.g., cypress, balsam, first, pines, etc.). In general, the wood, or wood chips, is charged to a treatment vessel, such as a digester vessel and cooked for a predetermined time with a cooking liquor.

Additionally, the digester additive composition may be delivered or transported to contact the wood using any method known in the art. For instance, the composition may be added directly to the treatment vessel, such as a digester vessel. Alternatively, the composition may be added to an input supply stream, such as one for the cooking liquor and then transported to contact the wood.

Illustratively, in a batch type digester, wood chips and a mixture of "black liquor", the spent liquor from a previous digester cook, and "white liquor", typically a solution of sodium hydroxide, sodium carbonate, sodium sulfate, sodium sulfide and various inorganic materials are pumped into the digester. In the cooking process, lignin, which binds the wood fiber together, is dissolved in the white liquor forming pulp and black liquor. Other suitable additives can be added to the white liquor as well.

The composition and/or method disclosed herein may provide a reduction in the amount of white liquor required. For instance, the white liquor required may be reduced by 0.1% or more, such as about 0.5% or more, such as 1% or more, such as 1.5% or more, such as 2% or more, such as 2.5% or more, such as 3% or more, such as 3.5% or more, such as 5% or more to 15% or less, such as 10% or less, such as 7% or less, such as 5% or less, such as 4% or less, such as 3% or less. Such average reduction in white liquor may be realized over the course of at least 3 plant runs, such as at least 4 plant runs, such as at least 5 plant runs, such as at least 6 plant runs, such as at least 7 plant runs, such as at least 10 plant runs.

The digester is sealed and the digester composition is heated to a suitable cook temperature under high pressure. After an allotted cooking time at a particular temperature and pressure in the digester, the digester contents (pulp and black liquor) are transferred to a holding tank. The pulp in the holding tank is transferred to the brown stock washers while the liquid (black liquor formed in the digester) is sent to the black liquor recovery area. The black liquor is evaporated to a high solids content in evaporators. The Kraft cook is highly alkaline, usually having a pH of 10 to 14, more particularly 12 to 14

Accordingly, the wood chips are subjected to alkaline reagents at elevated temperatures and pressures in a treatment vessel, such as a digester vessel, to produce a pulp. Generally, temperatures range from about 200° F. to about 500° F., such as from about 250° F. to about 350° F. and pressures range from about 60 psi/g to about 130 psi/g. Digestion time may range from 30 minutes to 10 hours, depending on the process conditions and the desired pulp/paper characteristics.

The reaction conditions present during the cook, or digestion, cause lignin—the amorphous polymeric binder found in wood fibers—to be hydrolyzed. Ideally, wood chips are digested only long enough to dissolve sufficient lignin to free the cellulosic wood fibers but maintain sufficient lignin intact to provide added strength to the paper. The pulping process attempts to maximize pulp yield, which is defined as the dry weight of pulp produced per unit dry weight of wood consumed.

After sufficient lignin has been dissolved to free the cellulosic wood fibers, the digester charge is blown into a receiving vessel, or blow tank. The sudden drop in pressure from the digester to the blow tank causes additional mechanical breakup of the wood fibers. In some papermaking applications, the residual lignin is removed to produce papers without the characteristic brown color of Kraft paper. In producing linerboard or Kraft paper, however, the lignin residue remains in the papermaking pulp so that the highest possible strength of wood pulp is achieved.

Ideally, each of the wood chips blown from the digester into the blow tank is broken down into separate wood fibers. In practice, however, some of the wood chips fail to completely separate due, in part, to the undissolved lignin remaining in the pulp. These unseparated particles are removed from the wood pulp by passing the pulp through a screen having openings of a predetermined size. In the pulping industry, the standard test screen employed is flat with 0.01 inch slots therethrough.

The materials that are recovered by this screening process are known as "rejects". The rejects include wood fibers that could be used to produce paper. Accordingly, it is highly desirable to decrease the amount of rejects. One method of lowering the amount of rejects is by increasing the digestion time or by creating more severe hydrolysis conditions. Such conditions, however, increase the costs involved and cause some of the cellulose in the wood chips to be hydrolyzed and rendered unusable.

After contact with liquor in the digester, the pulp is treated in one or more washing steps. In general, the temperatures in the digestion and washing stages typically vary from about 250° F. to 340° F. and 100° F. to 200° F., respectively. After washing, the pulp may be subjected to further bleaching or purification treatments as desired before being sheeted and dried, or prepared for sale, or further utilized in making paper.

A Kappa number corresponds directly to the amount of lignin remaining in the pulp. Generally, the higher the Kappa number, the more lignin present in the pulp and, therefore, the higher the pulp yield. The Kappa number generally decreases as the digestion time is increased or the alkalinity of the cooking liquor is increased. The goal in such Kraft papermaking processes is to retain as much lignin as possible in order to enhance strength and to reduce the cost, while maintaining the uniformity of the cook. More uniform cooks result in a decreased percentage of rejects and, thereby, reduce costs for running paper mills.

Cooking, or digestion, of the pulp may be terminated when the amount of rejects in the pulp is reduced to an acceptable level. Substantial yield and quality advantages are achieved if the wood chips are cooked to a higher lignin content. As a result, an increase in a Kappa number target by the use of thinner chips can result in a substantial cost savings. However, the thickness of chips obtainable on a commercial scale is always variable. A major portion of the total rejects frequently originate from a relatively small fraction of the chips having the greatest thickness. The objective in many pulping processes is to achieve a lower percentage of rejects.

After one or more washing steps, the pulp may be subjected to bleaching or purification treatments as desired before being sheeted and dried, or prepared for sale, or further utilized in making paper. Such bleaching and/or purification processes are known in the art.

Generally, bleaching may be performed using hydrogen peroxide. Hydrogen peroxide can be decomposed using catalysts, such as transition metals. These transition metals may include iron, manganese, and copper. The composition and/or method disclosed herein may provide a reduction in the amount of transition metals, such as manganese, required. For instance, the transition metals, such as manganese, iron, and/or copper, required may be reduced by 5% or more, such as 8% or more, such as 10% or more, such as 15% or more, such as 20% or more, such as 25% or more, such as 28% or more, such as 30% or more, such as 40% or more, such as 50% or more, such as 60% or more to 80% or less, such as 70% or less, such as 60% or less, such as 50% or less, such as 50% or less, such as 40% or less, such as 35% or less, such as 30% or less, such as 20% or less, such as 15% or less. Such average reduction in transition metals, such as manganese, iron, and/or copper, may be realized over the course of at least 2 plant runs, such as at least 3 plant runs, such as at least 4 plant runs, such as at least 5 plant runs. In addition, such reduction may be based on the decker and/or final bleaching.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part.

Furthermore, those of ordinary skill in the art will appreciate that the foregoing description is by way of example only, and is not intended to limit the invention so further described in such appended claims.

The invention claimed is:

1. A digester additive composition comprising,
   a first surfactant comprising an anionic surfactant, a derivative thereof, a salt thereof, or any combination thereof, and
   a second surfactant comprising an ester derivative of a polyoxyalkylene glycol wherein the ester derivative is obtained from an acid having from 12 to 25 carbon atoms.

2. The composition according to claim 1, wherein the second surfactant comprises the ester derivative of a polyoxyalkylene glycol and wherein the alkylene comprises from 2 to 5 carbon atoms.

3. The composition according to claim 1, wherein the second surfactant comprises an ester derivative of a polyethylene glycol-polypropylene glycol copolymer.

4. The composition according to claim 1, wherein the second surfactant comprises an ester derivative of a polyethylene glycol-polypropylene glycol copolymer.

5. The composition according to claim 1, wherein the second surfactant comprises a diester derivative of a polyethylene glycol-polypropylene glycol copolymer.

6. The composition according to claim 1, wherein the ester derivative is obtained from an acid having from 15 to 25 carbon atoms.

7. The composition according to claim 1, wherein the ester derivative is obtained from oleic acid.

8. The composition according to claim 1, wherein the ester derivative of the polyoxyalkylene glycol includes an ester derivative of a polyoxyalkylene glycol having a molecular weight of from about 1,000 g/mol to about 5,000 g/mol and a hydrophile percent of greater than 10% to less than about 35%, an ester derivative of a polyoxyalkylene glycol having a molecular weight of from 10,000 g/mol to about 15,000 g/mol and a hydrophile percent of greater than about 60% to less than about 80%, or a mixture thereof.

9. The composition according to claim 1, wherein the sulfonic acid comprises a benzenesulfonic acid.

10. The composition according to claim 1, wherein the first surfactant comprises a derivative of a sulfonic acid.

11. The composition according to claim 10, wherein the derivative comprises an alkyl derivative.

12. The composition according to claim 11, wherein the alkyl derivative comprises from 8 carbon atoms to 16 carbon atoms.

13. The composition according to claim 1, wherein the first surfactant comprises a salt of sulfonic acid or a derivative thereof.

14. The composition according to claim 13, wherein the salt comprises an alkali metal salt.

15. The composition according to claim 14, wherein the alkali metal comprises sodium or potassium.

16. The composition according to claim 1, wherein the first surfactant comprises dodecylbenzenesulfonic acid or a salt thereof.

17. The composition according to claim 1, wherein the first surfactant comprises a benzenesulfonic acid and a second sulfonic acid, wherein the second sulfonic acid is not a benzenesulfonic acid.

18. The composition according to claim 17, wherein the second sulfonic acid is an aromatic sulfonic acid.

19. The composition according to claim 1, wherein the first surfactant comprises a sulfonic acid, a sulfate, a carboxylate, a phosphate, a derivative thereof, a salt thereof, or a combination thereof.

\* \* \* \* \*